US009815878B2

(12) United States Patent
Tsao et al.

(10) Patent No.: US 9,815,878 B2
(45) Date of Patent: Nov. 14, 2017

(54) USE OF PEDF-DERIVED POLYPEPTIDES FOR PREVENTING AND/OR AMELIORATING SKIN AGING

(71) Applicants: Yeou-Ping Tsao, Taipei (TW); Tsung-Chuan Ho, Taipei (TW)

(72) Inventors: Yeou-Ping Tsao, Taipei (TW); Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 14/429,681

(22) PCT Filed: Sep. 19, 2012

(86) PCT No.: PCT/CN2012/081588
§ 371 (c)(1),
(2) Date: Mar. 19, 2015

(87) PCT Pub. No.: WO2014/043861
PCT Pub. Date: Mar. 27, 2014

(65) Prior Publication Data
US 2015/0232523 A1   Aug. 20, 2015

(51) Int. Cl.
| | |
|---|---|
| A61K 38/17 | (2006.01) |
| A61K 38/10 | (2006.01) |
| C07K 14/47 | (2006.01) |
| C07K 14/435 | (2006.01) |
| C07K 7/08 | (2006.01) |
| A61Q 19/08 | (2006.01) |
| A61K 8/64 | (2006.01) |
| C07K 14/475 | (2006.01) |
| A61M 37/00 | (2006.01) |
| A61K 38/57 | (2006.01) |

(52) U.S. Cl.
CPC .............. *C07K 14/475* (2013.01); *A61K 8/64* (2013.01); *A61K 38/10* (2013.01); *A61K 38/17* (2013.01); *A61K 38/57* (2013.01); *A61M 37/00* (2013.01); *A61M 37/0092* (2013.01); *A61Q 19/08* (2013.01); *C07K 7/08* (2013.01); *C07K 14/435* (2013.01); *C07K 14/47* (2013.01); *A61K 2800/78* (2013.01); *A61M 2037/0007* (2013.01)

(58) Field of Classification Search
None
See application file for complete search history.

(56) References Cited

U.S. PATENT DOCUMENTS

2009/0069241 A1   3/2009   Barnstable et al.
2010/0047212 A1   2/2010   Farinas Gomez et al.

FOREIGN PATENT DOCUMENTS

| | | |
|---|---|---|
| CN | 101977626 A | 2/2011 |
| CN | 102690344 A | 9/2012 |
| EP | 2508196 A1 | 10/2012 |
| JP | 2007-509984 A | 4/2007 |
| WO | 2005/041887 A2 | 5/2005 |
| WO | 2009/093119 A2 | 7/2009 |
| WO | 2014/023007 A1 | 2/2014 |
| WO | 2014/040302 A1 | 3/2014 |
| WO | 2014/043871 A1 | 3/2014 |

OTHER PUBLICATIONS

Mueller et al., Mol. Cancer Res., 2009, vol. 7(7):1078-1085.*
International Search Report issued in PCT/CN2012/081588 dated Jul. 4, 2013 (5 pages).
Official Action dated Mar. 29, 2016, by the Japan Patent Office in related Japanese Patent Application No. JP 2015-532263, with Google English machine translation (8 pages).
Extended European Search Report dated Feb. 12, 2016, issued by the European Patent Office in related European Patent Application No. EP-12885035.1 (7 pages).
EK, Eugene T.H., et al., "PEDF-Derived Synthetic Peptides Exhibit Antitumor Activity in an Orthotopic Model of Human Osteosarcoma"; Journal of Orthopaedic Research, vol. 25, No. 12, Dec. 1, 2007 (Dec. 1, 2007); XP055247609, ISSN: 0736-0266, DOI: 10.1002/jor.20434; pp. 1671-1680.
Francis, Mary Kay, et al., "Loss of EPC-1/PEDF Expression During Skin Aging In Vivo"; Journal of Investigative Dermatology, vol. 122, No. 5, May 1, 2004 (May 1, 2004); XP055247641, ISSN: 0022-202X, DOI: 10.1111/j.0022-202X.2004.22510.x; pp. 1096-1105.
Patent Examination Report No. 1 (Office Action) dated Jun. 30, 2016, by the Australian Patent Office in related Australian Patent Application No. 2012390200 (8 pages).
Office Action issued in Korean Application No. 10-2015-7009722; dated Aug. 19, 2016 (10 pages).
Notification of Final Rejection (Office Action) dated Mar. 27, 2017, issued by the Korean Intellectual Property Office (KIPO) in corresponding Korean Patent Application No. KR 10-2015-7009722, with English translation (10 pages).
First Office Action dated Feb. 16, 2017, issued by The State Intellectual Property Office of the Peoples Republic of China in corresponding Chinese Patent Application No. CN-201280077079.7, with USPTO Global Dossier English translation (13 pages).
Francis, Mary K., et al., "Loss of EPC-1/PEDF Expression During Skin Aging In Vivo"; The Society for Investigative Dermatology, Inc., vol. 122, No. 5, May 2004; pp. 1096-1105.
Final Office Action dated Mar. 7, 2017, issued by the Japan Patent Office in corresponding Japanese Patent Application No. JP 2015-532263, with Google English machine translation (10 pages).
Notice of Grounds for Preliminary Rejection (Office Action) dated Jul. 26, 2017, issued by the Korean Intellectual property Office (KIPO) in corresponding Korean Patent Application No. KR 10-2015-7009722, with English translation (6 pages.

* cited by examiner

*Primary Examiner* — Xiaozhen Xie
(74) *Attorney, Agent, or Firm* — Osha Liang LLP

(57) ABSTRACT

A method for preventing and/or ameliorating skin aging in a subject includes administering to the subject in need of such treatments a synthetic peptide, which has an amino acid sequence that has 20-39 amino acid residues. The synthetic peptide has at least 20 consecutive residues that has at least 90% amino acid sequence identity to residues 11-30 of SEQ ID NO: 1.

20 Claims, 3 Drawing Sheets

SEQUENCE LISTING

<160> NUMBER OF SEQ ID NOS: 15

<210> SEQ ID NO 1
<211> LENGTH: 39
<212> TYPE: PRT
<213> ORGANISM: Artificial Sequence
<220> FEATURE:
<223> OTHER INFORMATION: synthetic peptide

<400> SEQUENCE: 1

-continued

```
Leu Ser Val Ala Thr Ala Leu Ser Ala Leu Ser Leu Gly Ala Glu Gln
1               5                   10                  15

Arg Thr Glu Ser Ile Ile His Arg Ala Leu Tyr Tyr Asp Leu Ile Ser
            20                  25                  30

Ser Pro Asp Ile His Gly Thr
        35

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Ala Leu Ser Ala Leu Ser Leu Gly Ala Glu Gln Arg Thr Glu Ser Ile
1               5                   10                  15

Ile His Arg Ala Leu Tyr Tyr Asp Leu Ile Ser Ser Pro Asp Ile His
            20                  25                  30

Gly Thr

<210> SEQ ID NO 3
<211> LENGTH: 29
<212> TYPE: PRT
<213> ORGANISM: Artificial Sequence
<220> FEATURE:
<223> OTHER INFORMATION: synthetic peptide

<400> SEQUENCE: 3

Ser Leu Gly Ala Glu Gln Arg Thr Glu Ser Ile Ile His Arg Ala Leu
1               5                   10                  15

Tyr Tyr Asp Leu Ile Ser Ser Pro Asp Ile His Gly Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: synthetic peptide

<400> SEQUENCE: 4

Glu Gln Arg Thr Glu Ser Ile Ile His Arg Ala Leu Tyr Tyr Asp Leu
1               5                   10                  15

Ile Ser Ser Pro Asp Ile His Gly Thr
            20                  25

<210> SEQ ID NO 5
<211> LENGTH: 24
<212> TYPE: PRT
<213> ORGANISM: Artificial Sequence
<220> FEATURE:
<223> OTHER INFORMATION: synthetic peptide

<400> SEQUENCE: 5

Ser Leu Gly Ala Glu Gln Arg Thr Glu Ser Ile Ile His Arg Ala Leu
1               5                   10                  15

Tyr Tyr Asp Leu Ile Ser Ser Pro
            20

<210> SEQ ID NO 6
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 6

Ser Leu Gly Ala Glu Gln Arg Thr Glu Ser Ile Ile His Arg Ala Leu
1               5                   10                  15

Tyr Tyr Asp Leu
            20

<210> SEQ ID NO 7
<211> LENGTH: 18
<212> TYPE: PRT
<213> ORGANISM: Artificial Sequence
<220> FEATURE:
<223> OTHER INFORMATION: synthetic peptide

<400> SEQUENCE: 7

Glu Gln Arg Thr Glu Ser Ile Ile His Arg Ala Leu Tyr Tyr Asp Leu
1               5                   10                  15

Ile Ser

<210> SEQ ID NO 8
<211> LENGTH: 29
<212> TYPE: PRT
<213> ORGANISM: Artificial Sequence
<220> FEATURE:
<223> OTHER INFORMATION: synthetic peptide

<400> SEQUENCE: 8

Ser Leu Gly Ala Glu His Arg Thr Glu Ser Val Ile His Arg Ala Leu
1               5                   10                  15

Tyr Tyr Asp Leu Ile Thr Asn Pro Asp Ile His Ser Thr
            20                  25

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Ser Leu Gly Ala Glu His Arg Thr Glu Ser Val Ile His Arg Ala Leu
1               5                   10                  15

Tyr Tyr Asp Leu
            20

<210> SEQ ID NO 10
<211> LENGTH: 44
<212> TYPE: PRT
<213> ORGANISM: Artificial Sequence
<220> FEATURE:
<223> OTHER INFORMATION: synthetic peptide

<400> SEQUENCE: 10

Val Leu Leu Ser Pro Leu Ser Val Ala Thr Ala Leu Ser Ala Leu Ser
1               5                   10                  15

Leu Gly Ala Glu Gln Arg Thr Glu Ser Ile Ile His Arg Ala Leu Tyr
                20                  25                  30

Tyr Asp Leu Ile Ser Ser Pro Asp Ile His Gly Thr
            35                  40
```

-continued

```
<210> SEQ ID NO 11
<211> LENGTH: 418
<212> TYPE: PRT
<213> ORGANISM: Homo sapiens

<400> SEQUENCE: 11
```

Met Gln Ala Leu Val Leu Leu Cys Ile Gly Ala Leu Leu Gly His
 1               5                  10                  15

Ser Ser Cys Gln Asn Pro Ala Ser Pro Pro Glu Glu Gly Ser Pro
                20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
                275                 280                 285

Ile Glu Glu Ser Leu Thr Ser Glu Phe Ile His Asp Ile Asp Arg Glu
                290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
                355                 360                 365

Ala Gly Thr Thr Pro Ser Pro Gly Leu Gln Pro Ala His Leu Thr Phe
370                 375                 380

-continued

```
Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
atcctggcca ccttcttctt                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tttctcggag cctgtcaact                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
aactttggca ttgtggaagg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
acacattggg ggtaggaaca                                              20
```

USE OF PEDF-DERIVED POLYPEPTIDES FOR PREVENTING AND/OR AMELIORATING SKIN AGING

CROSS REFERENCE TO RELATED APPLICATIONS

This is a national phase application based on PCT/CN2012/081588, filed on Sep. 19, 2012, the disclosure of which is incorporated by reference in its entirety.

BACKGROUND OF THE INVENTION

1. Field of the Invention

The present disclosure relates to the prevention and/or amelioration of skin aging. In particular, the disclosed invention relates to the use of PEDF-derived polypeptides for preventing and/or ameliorating skin aging.

2. Description of Related Art

Human skin, like other living tissues, ages with time. Skin aging leads to the formation of wrinkles and fine lines, thinning of the skin, skin discoloration or hyperpigmentation, and loss of firmness and elasticity. Depending on the cause, skin aging can be classified into intrinsic aging and extrinsic aging. Intrinsic aging, or chronologic aging, affects almost all internal organs, and is primarily regulated by the genetic makeup of the subject. Extrinsic aging is the result of exposure to various environmental factors, primarily ultraviolet (UV) irradiation, and hence, it is often referred to as photoaging. In the areas exposed to the sun, such as the face, neck, and backs of the hands, the combination of intrinsic aging and photoaging damage may result in changes that are more noticeable.

Collagen is a fibrous, extracellular, insoluble protein that constitutes a major component of connective tissues. Among the various types of collagen, types I and III are of major relevance. Type I collagen is the major structural protein in human skin, comprising greater than 90% of its dry weight, whereas type III collagen, also widely distributed throughout the body, predominates in fetal tissues. As the skin ages, both the overall collagen content and the ratio of type I to type III collagen declines, and the extracellular matrix (ECM) becomes disorganized. For example, both intrinsic aging and ultraviolet B (UVB) exposure diminish the renewal of collagen fibres (in particular, type I collagen). Also, UVB exposure up-regulates the production of several collagen-degrading enzymes known as matrix metalloproteinases (MMP). MMPs in humans, specifically collagenase and gelatinase, are induced within hours of UVB exposures. All those events likely result in the alteration of the dermal extracellular matrix composition.

There are many treatments available for aged skins. For example, the importance of collagen in the aging process has led to the development of many collagen-containing topical products. Other components such as retinoic acid, vitamin C and hyaluronic acid are used in cosmetics owing to the claims that they can stimulate collagen synthesis. Some cosmetic procedures (e.g., laser skin resurfacing) are also effective for reducing facial wrinkles and skin irregularities.

Despite the number of solutions that have been proposed to reduce signs of aging, or to stimulate skin renewal, none of them is capable of evoking the intrinsic repair mechanisms of the skin (i.e., collagen synthesis). In view of the foregoing, there remains a need in the art for means that effectively treats skin aging, in particular, photoaging of the skin.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based, at least, on the finding that synthetic peptides derived from pigment epithelium-derived factor (PEDF) may stimulate collagen synthesis, promote dermal fibroblast proliferation, and down-regulate UVB-induced MMP-1 expression, and hence they are effective in preventing and/or ameliorating skin aging in a subject. The PEDF-derived synthetic peptides of this invention are, therefore, useful as an agent or a medicament against skin aging.

Accordingly, in one aspect, the present disclosure is directed to a synthetic peptide for preventing and/or ameliorating skin aging in a subject.

According to embodiments of the present disclosure, the synthetic peptide is 20-39 amino acid residues in length, and has an amino acid sequence that is at least 80% identical to SEQ ID NO: 1. Also, the amino acid sequence comprises at least 20 consecutive residues, which is at least 90% identical to residues 11-30 of SEQ ID NO: 1, such that the synthetic peptide is useful in preventing and/or ameliorating skin aging in a subject.

According to optional embodiments of the present disclosure, at least 4 consecutive residues of the synthetic peptide are identical to residues 11-14 of SEQ ID NO: 1. Non-limiting examples of such synthetic peptides include those respectively having an amino acid sequence of SEQ ID NO: 1 (39-mer), SEQ ID NO: 2 (34-mer), SEQ ID NO: 3 (29-mer), SEQ ID NO: 5 (24-mer), SEQ ID NO: 6 (20-mer), SEQ ID NO: 8 (MO 29-mer), and SEQ ID NO: 9 (MO 20-mer). In some embodiments of the present disclosure, the amino acid sequence of the synthetic peptide is SEQ ID NO: 3 (29-mer), SEQ ID NO: 5 (24-mer), or SEQ ID NO: 6 (20-mer).

According to various embodiments of the present disclosure, the skin aging is caused by UV irradiation.

According to various embodiments of the present disclosure, the subject may be any animal classified as a mammal, including human.

In another aspect, the present disclosure is directed to a pharmaceutical composition for preventing and/or ameliorating skin aging in a subject. The subject may be any animal classified as a mammal, including human.

According to one embodiment of the present disclosure, the pharmaceutical composition comprises a synthetic peptide according to any of the above-mentioned aspect/embodiments, and the synthetic peptide is present in an effective amount sufficient to treat skin aging in the subject. The pharmaceutical composition also comprises a pharmaceutically acceptable excipient for the synthetic peptide.

In certain optional embodiments, the pharmaceutical composition further comprises at least on penetration enhancer to promote the flux of the present synthetic peptide or pharmaceutical composition.

In various embodiments of the present disclosure, the pharmaceutical composition may be formulated into a solution, spray, aerosol, foam, cream, lotion, ointment, gel, or patch.

In yet another aspect, the present invention is directed to a method for preventing and/or ameliorating skin aging in a subject. The subject may be any animal classified as a mammal, including human.

In one embodiment, the method comprises administering to the subject an effective amount of the synthetic peptide according to any of the above-mentioned aspect/embodiments, such that the synthetic peptide is transdermally delivered to the dermis of the subject.

According to optional embodiments, the synthetic peptide is formulated into a pharmaceutical composition according to the above-mentioned aspect/embodiments of the present disclosure. In one example, the present pharmaceutical composition may be topically administered to the skin of the subject. In optional embodiments, the method further comprises the step of applying an external stimulus (e.g., a mechanical, electrical, thermal, ultrasonic, or radio frequency stimulus) to the skin of the subject before, concurrently with, or after the topical administration of the pharmaceutical composition to promote the transdermal delivery of the synthetic peptide or pharmaceutical composition. Still optionally, the pharmaceutical composition may further comprise at least on penetration enhancer to promote the flux of the present synthetic peptide or pharmaceutical composition.

According to certain embodiments of the present disclosure, the skin aging is caused by UV irradiation.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The present description will be better understood from the following detailed description read in light of the accompanying drawings.

DESCRIPTION

Figure 1:
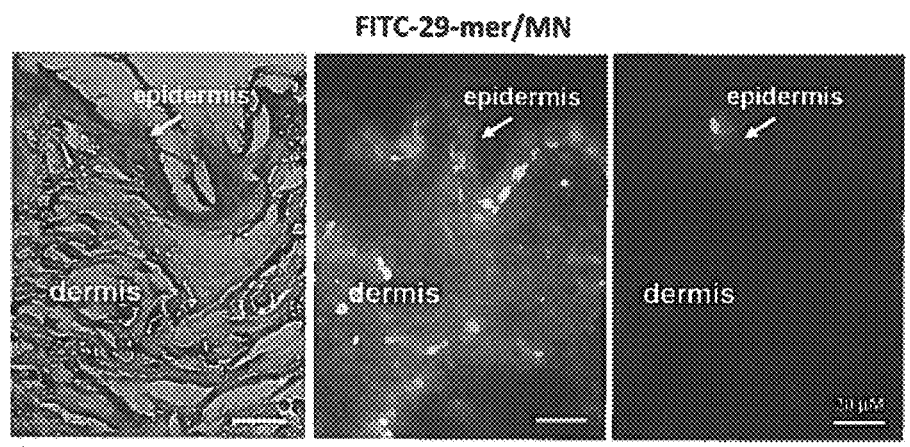
FIG. 1 provides an image of an H&E stained section (left panel) and fluorescent images (middle and right panels) of skin specimens according to one working example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the entire application (including the specification, examples, and appended claims) are collected here. Unless otherwise defined herein, scientific and technical terminologies employed in the present disclosure shall have the meanings that are commonly understood and used by one of ordinary skill in the related art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "peptide" denotes a polymer of amino acid residues. By the term "synthetic peptide" as used herein, it is meant a peptide that does not comprise an entire naturally occurring protein molecule. The peptide is "synthetic" in that it may be produced by human intervention using such techniques as chemical synthesis, recombinant genetic techniques, or fragmentation of the whole protein or the like. Throughout the present disclosure, the positions of any specified amino acid residues within a peptide are numbered starting from the N terminus of the peptide.

As used herein, "proliferating" and "proliferation" refers to an increase in the number of cells in a population by means of cell division.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "treating" as used herein refers to the application or administration of the synthetic peptide or pharmaceutical composition of the present disclosure to a subject, who has sign(s) of skin aging or a predisposition toward skin aging, with the purpose to partially or completely alleviate, ameliorate, relieve, delay onset of, inhibit progression of, reduce severity of, and/or reduce incidence of one or more sign(s) or features related to skin aging. Treatment is generally "effective" if one or more symptoms or clinical markers are reduced as that term is defined herein.

The term "effective amount" as used herein refers to the quantity of a component which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects.

The terms "application" or "administration" are used interchangeably herein to refer means providing a synthetic peptide or a pharmaceutical composition of the present invention to a subject to prevent and/or ameliorate skin aging. According to various embodiments of the present disclosure, transdermal delivery is a preferred delivery route. For example, the synthetic peptide or pharmaceutical composition of the present invention is topically applied to the skin of the subject such that the synthetic peptide or the present pharmaceutical composition reaches the target site (e.g., dermis) so as to prevent and/or ameliorate skin aging.

The term "excipient" as used herein means any inert substance (such as a powder or liquid) that forms a vehicle/carrier for the synthetic PEDF peptide(s) of the present disclosure. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

As used herein, a "pharmaceutically acceptable" component is one that is suitable for use with humans and/or animals without undue adverse side effects (such as toxicity, irritation, and allergic response) commensurate with a reasonable benefit/risk ratio. Also, each excipient must be "acceptable" in the sense of being compatible with the other ingredients of the pharmaceutical formulation. The carrier can be in the form of a solid, semi-solid, or liquid diluent, cream or a capsule.

The term "subject" refers to a mammal including the human species that is treatable with the synthetic peptides, compositions, and/or methods of the present invention. The term "subject" is intended to refer to both the male and female gender unless one gender is specifically indicated.

As used herein, the term "transdermal" means passage of an active agent (e.g., the present synthetic peptides or pharmaceutical compositions) through the epidermis to the dermis.

Pigment epithelium-derived factor (PEDF) is a multifunctional secreted protein that has anti-angiogenic, anti-tumorigenic, and neurotrophic functions. Human PEDF protein (SEQ ID NO: 11) is a secreted protein of roughly 50 kDa size and 418 amino acids in length. A 34-mer fragment (residues 44-77) and a 44-mer fragment (residues 78-121; SEQ ID NO: 10) of PEDF have been identified to have anti-angiogenic and neurotrophic properties, respectively.

The present disclosure is based, at least, on the finding that synthetic peptides derived from the 44-mer PEDF may protect the skin from the damage of skin aging via a variety of mechanisms. Examples of the present disclosure demonstrate that the synthetic peptide may increase the collagen level in the dermis, induce the proliferation of dermal fibroblasts, and reduce the expression of MMP-1 (a UVB-inducible collagenase). Another inventive feature of the present invention lies in that the synthetic peptides are much shorter (39 amino acid residues at most) than the full-length PEDF and thus overcomes the limitations associated with the clinical use of conventional protein drugs, including high manufacturing cost, low bioavailability, and poor pharmacokinetics. Accordingly, the present synthetic peptides are useful for preventing and/or ameliorating skin aging.

Thus, in one aspect, the present disclosure is directed to a synthetic peptide for preventing and/or ameliorating skin aging in a subject.

According to embodiments of the present disclosure, the synthetic peptide has 20-39 amino acid residues in length, and has at least 80% amino acid sequence identity with the amino acid sequence of LSVATALSALSLGAEQRTESIIHRALYYDLISSPDIHGT (SEQ ID NO: 1). For example, the synthetic peptide may have an amino acid sequence identity of about 80, 81, 82, 83, 84, 85, 86, 87, 88, 89, 90, 91, 92, 93, 94, 95, 96, 97, 98, 99, or 100 percent with SEQ ID NO: 1. Also, the synthetic peptide comprises at least 20 consecutive residues that are at least 90% identical to residues 11-30 of SEQ ID NO: 1. Specifically, the 20 consecutive amino acid residues may have about 90, 91, 92, 93, 94, 95, 96, 97, 98, 99, or 100 percent amino acid sequence identity with residues 11-30 of SEQ ID NO: 1.

In one embodiment, the synthetic peptide has the sequence of SEQ ID NO: 1, which has 39 amino acids in length. This synthetic peptide is referred to as 39-mer in the description hereinbelow. This 39-mer peptide corresponds to residues 83-121 of human PEDF and hence is a short variant derived from the known PEDF 44-mer (corresponding to residues 78-121 of PEDF).

Prior experiments conducted by the present inventors, such as those disclosed in the co-pending application U.S. Ser. No. 13/428,996 (the entirety of which is incorporated herein by reference) and experiments provided hereinbelow, reveal that several short, synthetic PEDF peptides derived from the 39-mer, are capable of preventing and/or ameliorating skin aging in a subject.

For example, based on experiments disclosed in both the prior application and the present application, a 34-mer synthetic peptide having the sequence of ALSALSLGAEQRTESIIHRALYYDLISSPDIHGT (SEQ ID NO: 2) is effective in preventing and/or ameliorating skin aging in a subject. This 34-mer peptide corresponds to residues 88-121 of human PEDF. According to the process for estimating percentage of sequence identity between any two given sequences provided above, the 34-mer has a 100% amino acid sequence identity to the 39-mer, and the $6^{th}$-$25^{th}$ amino acid residues of the 34-mer has a 100% amino acid sequence identity to the amino acid residues 11-30 of the 39-mer.

Additionally, according to various examples hereinbelow, a 29-mer synthetic peptide having the sequence of SLGAEQRTESIIHRALYYDLISSPDIHGT (SEQ ID NO: 3) has been confirmed to be effective in preventing and/or ameliorating skin aging in a subject. This 29-mer peptide corresponds to residues 93-121 of human PEDF with a 100% amino acid sequence identity to the 39-mer. Also, the $1^{st}$-$20^{th}$ amino acid residues of the 29-mer has a 100% amino acid sequence identity to the amino acid residues 11-30 of the 39-mer.

In some examples, a 24-mer has been confirmed to be effective in preventing and/or ameliorating skin aging in a subject. The 24-mer has the sequence of SLGAEQRTESIIHRALYYDLISSP (SEQ ID NO: 5), which corresponds to residues 93-116 of human PEDF. This 24-mer peptide has a 100% amino acid sequence identity to the 39-mer in which the first twenty amino acid residues thereof has a 100% amino acid sequence identity to the amino acid residues 11-30 of the 39-mer.

In other examples, it has been established that a 20-mer may prevent and/or ameliorating skin aging in a subject. The 20-mer has the sequence of SLGAEQRTESIIHRALYYDL (SEQ ID NO: 6), which corresponds to residues 93-112 of human PEDF. This 20-mer peptide is completely identical to the amino acid residues 11-30 of the 39-mer (100% amino acid sequence identity), and has a 100% amino acid sequence identity to the 39-mer.

Two synthetic peptides derived from mouse PEDF may also prevent and/or ameliorating skin aging in a subject based on experiments disclosed in both the prior application and the present application. The first mouse-derived peptide is referred to as "Mo 29-mer" in the present disclosure. The Mo 29-mer has a sequence of SLGAEHRTESVIHRALYYDLITNPDIHST (SEQ ID NO: 8), which has a 83% amino acid sequence identity to 39-mer, and the first 20 amino acid residues thereof has a 90% amino acid sequence identity to the 11-30 amino acid residues of the 39-mer. Another mouse-derived peptide, Mo 20-mer has a sequence of SLGAEHRTESVIHRALYYDL (SEQ ID NO: 9). The Mo 20-mer has a 90% amino acid sequence identity to either the 39-mer or the 11-30 amino acid residues of the 39-mer.

Optionally, the synthetic peptide comprises 4 consecutive residues identical to residues 11-14 of SEQ ID NO: 1. It is believed that residues 11-14 (i.e., SLGA) of SEQ ID NO: 1 play an important role in maintaining the biological function of the short PEDF peptides. For example, according to various examples provided below, an 18-mer peptide (EQRTESIIHRALYYDLIS; SEQ ID NO: 7) without the SLGA residues fails to elicit any protection against skin aging in a subject. Also, based on experiments disclosed in both the prior application and the present application, it is suggested that a 25-mer peptide (EQRTESIIHRALYYDLISSPDIHGT; SEQ ID NO: 4) without the SLGA residues would not prevent and/or ameliorate skin aging in a subject.

The synthetic Peptides of the invention can be synthesized by commonly used methods such as t-BOC or FMOC protection of alpha-amino groups. Both methods involve stepwise syntheses whereby a single amino acid is added at each step starting from the C terminus of the peptide. Peptides of the present invention can also be synthesized by the well-known solid phase peptide synthesis methods.

Other synthetic peptides with conservative variation with respect to the 39-mer are also contemplated. The term "conservative variation" as used herein denotes the replacement of an amino acid residue by another, biologically similar residue. Examples of conservative variations include the substitution of one hydrophobic residue such as isoleucine, valine, leucine, or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

According to various embodiments of the present disclosure, the skin aging may be caused by UV (in particular, UVB) irradiation.

According to various embodiments of the present disclosure, the subject may be any animal classified as a mammal, including human.

The synthetic peptides according to above-mentioned embodiments may be formulated into pharmaceutical compositions for preventing and/or ameliorating skin aging in a subject, which falls within other aspects of the present disclosure.

According to one embodiment of the present disclosure, the pharmaceutical composition comprises a synthetic peptide according to any of the above-mentioned aspect/embodiments, and the synthetic peptide is present in an effective amount sufficient to prevent and/or ameliorate skin aging in the subject. The pharmaceutical composition also comprises a pharmaceutically acceptable excipient for the synthetic peptide.

The pharmaceutical composition is prepared in accordance with acceptable pharmaceutical procedures, such as described in Remington's Pharmaceutical Sciences, $17^{th}$ edition, ed. Alfonoso R. Gennaro, Mack Publishing Company, Easton, Pa. (1985).

The choice of a pharmaceutically acceptable excipient to be used in conjunction with a synthetic peptide is basically determined by the way the pharmaceutical composition is to be administered. According to one optional embodiment of the present disclosure, the pharmaceutical composition or the synthetic peptide contained therein may be transdermally delivered to the dermis of the subject, and hence, an excipient suitable for that means is used. A wide variety of dermatologically acceptable inert excipients well known to the art may be employed. Typical inert excipients may be, for example, water, ethyl alcohol, polyvinyl pyrrolidone, propylene glycol, mineral oil, stearyl alcohol, and gel-producing substances.

In an alternative approach, the synthetic peptide may be first encapsulated with a vesicle-forming vehicle (such as liposome, microsphere, or nanosome) and then formulated into a desired dosage form. These vesicle-forming vehicles may facilitate the transdermal delivery rate of the present synthetic peptide. In addition, they may provide a sustained-release dosage form to ensure a more prolonged therapeutic action of the treatment.

Alternatively or additionally, the pharmaceutical composition may further comprise an optional penetration enhancer capable of promoting the transdermal delivery rate of the synthetic peptide or the pharmaceutical composition. For example, the penetration enhancers may act to disrupt the highly ordered structure of stratum corneum lipid, interact with the intercellular protein(s), or improve the partition of the drug, co-enhancer or vehicle into the stratum corneum. Examples of penetration enhancers include, but are not limited to, sulphoxides (e.g., dimethyl sulfoxide (DMSO) and dimethylformamide (DMF)), azones (e.g., 1-dodecylazacycloheptan-2-one), pyrrolidones (e.g., N-methyl-2-pyrolidone), oils (e.g., terpenes and L-menthol), oxazolidinones (e.g., 4-decyloxazolidin-2-one), fatty acids (e.g., lauric acid, myristic acid and capric acid), glycols (e.g., diethylene glycol and tetraethylene glycol), surfactants (e.g., polyoxyethylene-2-oleyl ether and polyoxy ethylene-2-stearly ether), pore-forming peptides (e.g., magainin), and cell-penetrating peptides (e.g., transportan and penetratin).

Still optionally, pharmaceutical compositions of the present invention can also comprise various pharmaceutically— (in particular, dermatologically-) acceptable additives well known to the art. Said additives include, but are not limited to, drying agent, anti-itch agents, anti-foaming agents, buffers, neutralizing agents, pH adjusting agents, coloring agents, discoloring agents, emollients, emulsifying agents, emulsion stabilizers, viscosity builders, humectants, odorants, preservatives, antioxidants, chemical stabilizers, thickening agents, stiffening agents, or suspending agents.

In various embodiments of the present disclosure, the pharmaceutical composition may be formulated in various dosage forms suitable for transdermal delivery, such as a solution, spray, aerosol, foam, cream, lotion, ointment, gel, or patch.

According to optional embodiments of the present disclosure, the synthetic peptide is present in the pharmaceutical composition in an amount of about 0.1-100 µM, and preferably, about 1-25 µM. For example, the concentration of the synthetic peptides may be about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 µM. Specifically, the concentration used in the working examples below on mice (weighing about 20 grams) is about 25 µM. Persons having ordinary skills could calculate the human equivalent dose (HEQ) for the present synthetic peptide or pharmaceutical composition based on the animal doses provided herein. For example, the US Food and Drug Administration (FDA) has issued guidance for industry titled "Estimating the Maximum Safe Starting Dose in Initial Clinical Trials for Therapeutics in Adult Healthy Volunteers."

In yet another aspect, the present invention is directed to a method for preventing and/or ameliorating skin aging in a subject. The subject may be any animal classified as a mammal, including human. According to principles and spirits of the present disclosure, the skin aging is caused by UV irradiation.

In one embodiment, the method comprises administering to the subject an effective amount of the synthetic peptide according to any of the above-mentioned aspect/embodiments such that the synthetic peptide is transdermally delivered to the dermis of the subject.

According to optional embodiments, the synthetic peptide is formulated into a pharmaceutical composition according to the above-mentioned aspect/embodiments of the present disclosure.

In one example, the present pharmaceutical composition may be topically administered to the skin of the subject, and the synthetic peptide or the pharmaceutical composition is transdermally delivered to the dermis of the subject with or without the aid of an external stimulus.

In the event where no external stimulus is applied, the pharmaceutical composition may be topically spread, smeared, massaged, sprayed, or otherwise applied onto the skin of the subject. In this case, the pharmaceutical composition may preferably comprise at least one optional penetration enhancer as discussed above. Alternatively or additionally, the synthetic peptide may be encapsulated and formulated as taught above to improve the transdermal delivery rate of the synthetic peptide.

Many external stimuli are known to increase the skin permeability to a compound (e.g., the present synthetic peptide). Such external stimuli include, but are not limited to, mechanical, electrical, thermal, ultrasonic, or radio frequency stimuli. In practice, the external stimuli may be applied to the skin before, concurrent with, or after the application of the pharmaceutical application. Similarly, the pharmaceutical composition or synthetic peptide that is delivered with the aid of such external stimuli may optionally comprise the penetration enhancer and/or vesicle-forming vehicle described above.

In one embodiment, a micro-structured applicator (such as a microneedle system or a microchannel system) is employed to provide a mechanical stimulus to the skin. The microneedle system may comprise multiple solid or hollow microneedles which are about 100-1000 µM tall. For the solid microneedle system, the present synthetic peptide or pharmaceutical composition is coated onto to the tips of each microneedle, and upon application, microneedles penetrate the stratum corneum and remain in the skin, thereby delivering the present synthetic peptide or pharmaceutical composition to the dermis. As to the hollow microneedle system, the pharmaceutical composition formulated in the liquid form is loaded into the internal cavity of each microneedle, and upon application microneedles penetrate the skin to allow for fluid flow from the device into the dermis of the skin. Alternatively, the present pharmaceutical composition is topically applied to the skin, and then a microchannel system having a plurality of microneedles is pressed against the skin such that the microneedles penetrate less than 100 microns into the skin, thereby creating a plurality of microchannels on the skin to allow the transdermal delivery of the pharmaceutical composition. Still alternatively, the present pharmaceutical composition is topically applied after the microchannels are created.

Additionally, the synthetic peptide or the topical pharmaceutical compositions according to optional embodiments of the present disclosure may be administered under specified conditions (e.g., a specific humidity or temperature). For example, the administration under a more humid and warm environment may facilitate the transdermal delivery rate of the synthetic peptide.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Materials

Dulbecco's modified Eagle's medium (DMEM), fetal bovine serum (FBS), 0.25% trypsin were purchased from Invitrogen (Carlsbad, Calif.). Light mineral oil, glycerol, dimethyl sulfoxide (DMSO), bovine serum albumin (BSA), 5-bromo-2'-deoxyuridine (BrdU), Hoechst 33258 dye, Hoechst 33342 dye, anti-β-actin antibody and other chemicals were all from Sigma-Aldrich (St. Louis, Mo.). Dispase II and collagenase I were obtained from Roche (Indianapolis, Ind.). Anti-BrdU antibody (GTX42641), anti-MMP-1 antibody, and anti-vimentin antibody (GTX100619) were purchased from GeneTex (Taipei, Taiwan). Anti-collagen 1A1 antibody was obtained from Santa Cruz Biotechnology (Santa Cruz, Calif.). All fluorescent dye-conjugated secondary antibodies were purchased from BioLegend (San Diego, Calif.). Hematoxylin and eosin (H&E) dyes were purchased from Merck (Rayway, N.J., USA).

FITC-conjugated 29-mer and other short synthetic PEDF peptides, including 29-mer (SEQ ID NO: 3), 24-mer (SEQ ID NO: 5), 20-mer (SEQ ID NO: 6), and 18-mer (SEQ ID NO: 7) were synthesized and modified by acetylation at the $NH_2$ termini and amidation at the COOH termini. The modified peptide were subsequently characterized by mass spectrometry (>95% purity) (GenScript (Piscataway, N.J.). Each PEDF-derived short synthetic peptide (the 29-mer, 24-mer, or 20-mer; herein below, PEDF peptide) was reconstituted in DMSO as stock (5 mM), and stored at −20° C. for further use.

Skin ointment was prepared by mixing white petrolatum (10% w/w), glycerol (10% w/w), and light mineral oil (1% w/w) in distilled water. For the preparation of the ointment containing the PEDF peptide, 5 μl of PEDF peptide stock was dissolved in 1 gram of ointment. As to ointment for used as the vehicle control, 5 μl of DMSO was dissolved in 1 gram of ointment.

Animals

All animals used in embodiments of the present disclosure were housed in an animal room under temperature control (24-25° C.) and 12:12 light-dark cycle. Standard laboratory chow and tap water were available ad libitum. The experiments procedures were approved by the Mackay Memorial Hospital Review Board (New Taipei City, Taiwan, R.O.C.) and were performed in compliance with national animal welfare regulations.

Isolation and Culture of Dermal Fibroblasts from Mouse Dermis

Full-thickness skin tissue was obtained from the dorsum of C57BL/6 mouse. The subcutaneous tissue was carefully dissected from the skin and washed three times in sterile phosphate-buffered saline (PBS). The tissue was then cut into small pieces (1-2 $mm^3$). After being digested with 0.1% dispase at 4° C. overnight, the epidermal layers were removed, and the remaining dermal parts were further digested with 0.1% collagenase I at 37° C. for another 4 hours. The digested cells were then collected by centrifugation (400 g for 5 minutes) and resuspended in high-glucose DMEM supplemented with 10% FBS, 2 mM L-glutamine, and 1% penicillin-streptomycin antibiotic mixture. Cells were seeded onto tissue-culture plates (Falcon Labware; NJ, USA) at $1 \times 10^3$ cells/$cm^2$ and maintained at 37° C. with 5% $CO_2$. After 24 hours, the medium was discarded to remove residual non-adherent cells, and cell culture was replenished with a fresh medium. For passage, near-confluent cells were harvested with 0.25% trypsin/EDTA.

Cell Culture of WS-1

Human skin fibroblast WS-1 cell line was obtained from Food Industry Research and Development Institute (Hsin-Chu, Taiwan). The WS-1 cells were maintained in a 37° C., 5% $CO_2$ humidified incubator as monolayers in culture flasks. They were grown in 10% FBS-DMEM supplemented with 2 mM L-glutamine, 0.1 mM non-essential amino acids, 1% penicillin/streptomycin. For passage, near-confluent cells were sub-cultured by 0.25% trypsin/EDTA.

Histology

The skin sample was fixed in 4% paraformaldehyde, dehydrated with graded ethanol series, and paraffinized. Tissues were sliced into 5-μm sections. Before use, fixed samples were de-paraffinized in xylene and rehydrated in a graded series of ethanol.

General histology was performed using hematoxylin and eosin (H&E) dye. Deparaffinized skin tissue sections were stained using Masson's Trichrome (Sigma-Aldrich, St. Louis, Mo.) according to the manufacturer's instructions; sections was examined and photographed by a Nikon Eclipse 80i light microscope (original magnification, ×400). For semi-quantitative analysis of collagen area, 10 fields from each slide were randomly selected under the light microscope, and the blue-stained area per entire area of the cross section ($mm^2/mm^2$) was measured using the Image-Pro Plus 4.5.1 system (Media Cybernetics).

Immunofluorescence and BrdU Staining

After fixing with 4% paraformaldehyde, cells were exposed to cold methanol for 2 minutes, and then treated with 1 N HCl at room temperature for 1 hour before performing immunofluorescence staining.

For animal study, BrdU was reconstituted in DMSO as stock (80 mM). 10 μl of BrdU stock mixed with 90 μl of PBS was intraperitoneally injected into mouse at 16 hours prior to euthanasia. Formalin-fixed, paraffin-embedded skin specimens were deparaffinized in xylene and rehydrated in a graded series of ethanol. The specimens were then exposed to 1 N HCl at room temperature for 1 hour for subsequent immunofluorescence study.

BrdU-labeled DNA was detected by polyclonal anti-BrdU antibody and rhodamine-conjugated donkey anti-rabbit IgG. Nuclei were counterstained with Hoechst 33258 (blue).

Immunoblot Analysis

Skin tissues were homogenized in ice-cold lysis buffer containing 20 mM HEPES (pH 7.4), 150 mM NaCl, 1% SDS, 1 mM ethylenediamine tetraacetic acid (EDTA), 5 mM phenylmethanesulfonyl fluoride (PMSF), and 1 mM dithiothreitol (DTT), 1% Triton X-100, with freshly added protease inhibitor cocktail (Roche, Indianapolis, Ind.). Homogenates were then centrifuged at 12,000 g for 30 minutes at 4° C., and supernatants were then collected and stored at −70° C. Protein contents in lysates were determined using the Bradford assay. Whole cell lysates were prepared using the above lysis buffer. Aliquots of the lysates were then resolved on a SDS-PAGE and then electrotransferred to polyvinylidene difluoride (PVDF) membranes (Millipore, Bedford, Mass., USA) and processed for immunoblot analysis.

Antibodies used in the immunoblot study included anti-type I collagen 1A1 antibody (1:1000 dilution), anti-MMP-1 antibody (1:500 dilution) and anti-β-actin antibody (1:10000 dilution). Proteins of interest were detected using the appropriate IgG-HRP secondary antibody and ECL reagent (Amersham, Arlington Heights, Ill., USA). X-ray films were scanned on a Model GS-700 Imaging Densitometer (Bio-Rad Laboratories, Hercules, Calif.) and analyzed using Labworks 4.0 software. For quantification, blots from at least three independent experiments were used.

RNA Extraction and Reverse Transcription—Polymerase Chain Reaction

The total RNA was extracted from cells using the TRIzol (Invitrogen) and treated with RNase-free DNase I (Qiagen, Santa Clarita, Calif.) to remove genomic DNA and then purified with an RNA purification kit (Dynabeads; Invitrogen). 1 µg of total RNA retrieved from primary dermal fibroblast was reverse-transcribed into cDNA by 200 units of expand Reverse-Transcriptase (Roche, Mannheim, Germany) in 20 µl of reaction buffer containing 0.25 µg of random primers and 0.8 mM dNTPs at 42° C. for 1 hour. 2 µl of the cDNA was used for the PCR reaction as templates. PCR was performed in a 30 µl volume containing 15 µl of EconoTaq® PLUS GREEN 2× Master Mix (Lucigen® Corp.), 1 µM of each primer and 2 µl of template DNA. cDNA was synthesized in an 18-22 cycle amplification reaction (denaturation, 20 s, 94° C.; annealing, 30 s, 57° C.; and polymerization, 40 s, 72° C.). The number of cycles for the primer set was chosen to be in the linear range of amplification. The sequences of specific PCR primers were mouse MMP-13 (accession number: NM_008607) sense, ATCCTGGCCACCTTCTTCTT (SEQ ID NO: 12); anti-sense, TTTCTCGGAGCCTGTCAACT (SEQ ID NO: 13); PCR product: 201 bp; and mouse glyceraldehyde 3-phosphate dehydrogenase (GAPDH; accession number: M32599) sense, AACTTTGGCATTGTGGAAGG (SEQ ID NO: 14); and anti-sense, ACACATTGGGGGTAGGAACA (SEQ ID NO: 15); PCR product: 223 bp.). The PCR products were electrophoresed in a 2% agarose gel containing ethidium bromide and visualized by UV illumination. The intensities of the PCR products were quantified densitometrically using a FUJI LAS-3000 system and Multi Gauge Ver. 1.01 software (Fujifilm, Tokyo, Japan).

Statistics

Results were expressed as the mean±standard error of the mean (SEM). One-way ANOVA was used for statistical comparisons. P<0.05 was considered significant, unless otherwise specified.

Example 1

Transdermal Delivery of PEDF Peptides

The Fluorescein (FITC)-conjugated 29-mer peptide was used to investigate the in vivo transdermal delivery of the present PEDF peptides.

First, the dorsal hair of 8-wk-old male C57BL/6 mice were removed using a melted wax/rosin mixture (1:1) under general anesthesia. On the next day, the ointment containing the FITC-conjugated 29-mer peptide (25 µM) was applied onto the dorsal skin of the mice, and then a microneedle patch (3M™ Microchannel Skin System; provided from 3M Singapore) was gently pressed against the dorsal skin so that the microneedles penetrated less than 100 microns into the skin (the FITC-29 mer/MN group). As to the control group (FITC-29 mer/CT), the mice received the ointment without subsequent microneedle treatment. Twenty-four hours later, the skin was harvested, fixed, cryosectioned and examined by fluorescent microscopy. Representative images (original magnification, ×400) of three independent experiments are provided in FIG. 1.

The H&E stained section in the left panel of FIG. 1 highlights the epidermis and dermis of the specimen. The fluorescence images in the middle and right panels of FIG. 1 illustrate the distribution of FITC-conjugated 29-mer across the skin. In particular, the highly recognizable green signal from the fluorescein across the epidermis and dermis in the FITC-29 mer/MN group indicates that the FITC-conjugated 29-mer peptide was successfully delivered to the dermis. By contrast, in the FITC-29 mer/CT group, the green signal was barely detectable in the dermis, while most fluorescein signal resided at the epidermis.

Example 2

PEDF Peptides Increase Dermal Collagen Content

Collagen is the major matrix component of the dermis and forms a tough fiber framework to provide the elastic property of the skin. This working example investigated whether the present PEDF peptides increase dermal collage content. Mice depilated as described in Example 1 were randomly assigned to several experimental groups and treated as follows. For each mouse, one side of the dorsal midline (about 2 $cm^2$) received 50 µl of ointment (the 29-mer, 20-mer, or DMSO-containing ointment) and a subsequent microneedle treatment; while the other side of the dorsal midline (about 2 $cm^2$) received 50 µl of the same ointment without the microneedle treatment. The treatment was given twice a week for two weeks, and the skin was left uncovered and harvested 14 days after the first treatment. Skin specimens were stained with Masson's trichrome stain (blue) for dermal collagen; representative images are provided in FIG. 2. The stained collagen area in the skin was quantified as taught above in the "Materials and Methods" section, and the results were normalized with the area of Vehicle/MN. The level of type I collagen (COL1A1) was investigated by the above-described immunoblot analysis, and the results were normalized with the level of the vehicle/CT group. Quantitative results are summarized in Table 1.

TABLE 1

| Treatment | Collagen Area (fold) | COL1A1 Level (fold) |
|---|---|---|
| Vehicle/CT | 1.0 ± 0.16 | 1 |
| Vehicle/MN | 1 | 1 ± 0.13 |
| 29-mer/MN | 1.7 ± 0.14* | 1.7 ± 0.24** |
| 20-mer/MN | 1.6 ± 0.11* | 1.8 ± 0.20** |

*$P < 0.05$ versus the Vehicle/MN group.
**$P < 0.002$ versus the Vehicle/CT group.

Figure 2:
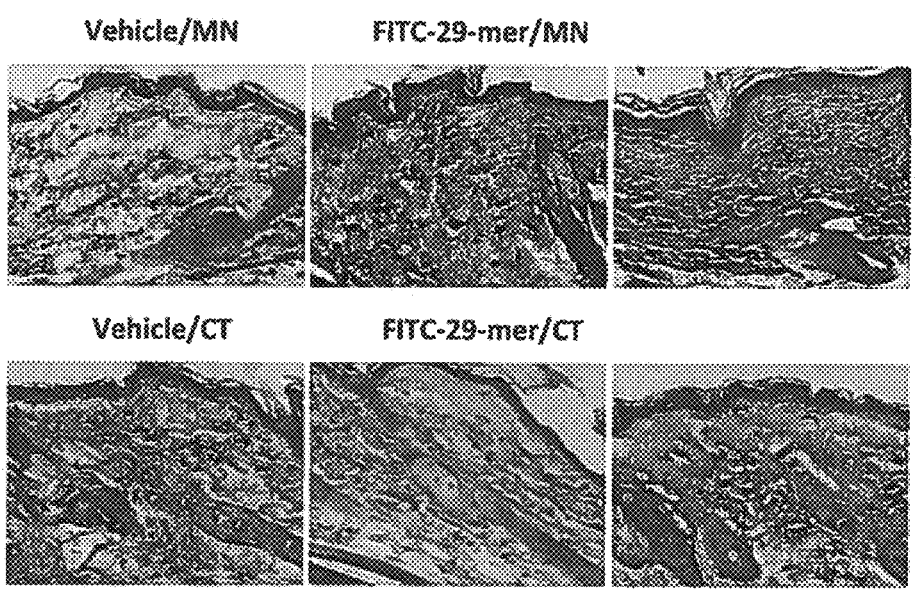
FIG. 2 provides representative images of skin tissue sections stained by Masson's trichrome to highlight the collagen fibres according to another working example of the present disclosure.

The images in FIG. 2 indicate that the treatment of 29-mer or 20-mer in combination with microneedle treatment will increase the collagen level in the dermis, as is evident from the more prominent blue stain in the 29-mer/MN and 20-mer/MN sections, when compared with the vehicle/MN section. Further, by comparing the vehicle/CT and vehicle/MN sections, we noted that the microneedle treatment alone has no effect on the level the collagen. Also, there is no significant difference in collagen levels among sections from vehicle/CT, 20-mer/CT, and 29-mer/CT, indicating that the collagen level does not vary significantly among the test subjects.

Type I collagen (COL1A1) is the major component of dermal collagen, and the immunoblot analysis indicated that the 29-mer/MN and 20-mer/MN treatments result in significant increase in the COL1A1 level, as compared with that of the control treatment (vehicle/CT).

Example 3

PEDF Peptides Promote Dermal Fibroblast Proliferation

Fibroblasts are the major collagen-producing cells in human skin, and hence, in vitro and in vivo analyses were carried out to evaluate the effects of the present PEDF peptides on the proliferation of dermal fibroblast.

Example 3.1

PEDF Peptides Promote Dermal Fibroblast Proliferation In Vitro

Figure 3:
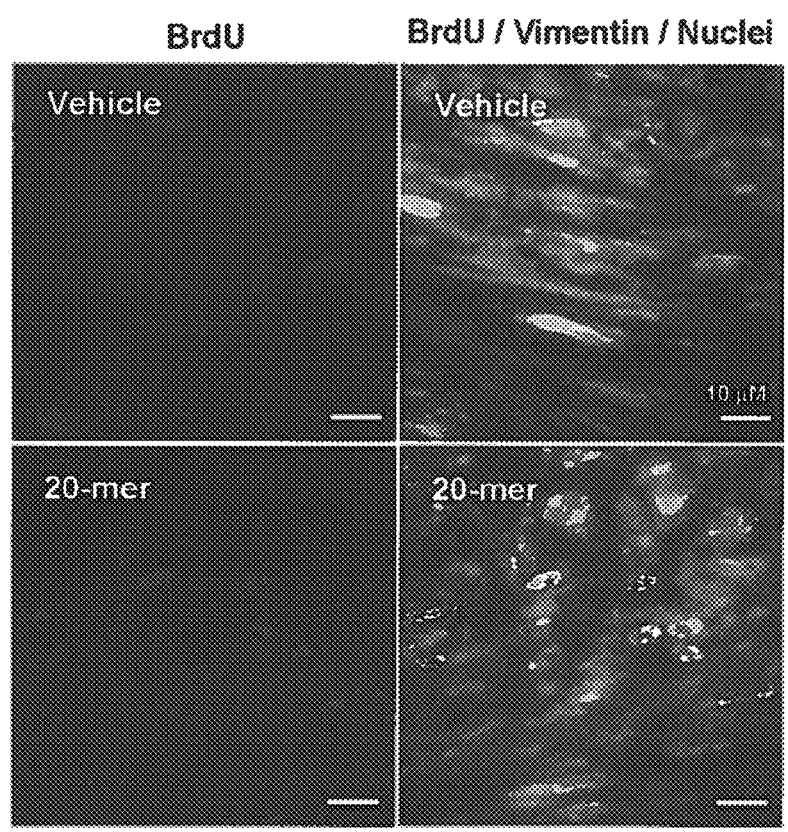
FIG. 3 provides representative immunostained images of primary dermal fibroblasts (vimentin: green; and BrdU: red), and merged to nuclear stained Hoechst 33258 (blue)

Primary mouse dermal fibroblasts were isolated and cultured as described in the "Materials and Methods" section. The dermal fibroblast at passage 2 were seeded at gelatin-coated slide in a 6-well plate at a density of $2 \times 10^5$ cells per well and cultured in growth medium (DMEM 10% FBS) for 24 hours before being replaced by a basal growth medium with 1% FBS only (control group) or with 1% FBS plus an additional 50 nM of PEDF-derived peptide (i.e., 29-mer, 24-mer, 20-mer, 18-mer, Mo 29-mer, or Mo 20-mer) for 24 hours. For BrdU labeling assay, BrdU (final concentration, 10 µM) was added to the culture for 2 hours. The fibroblasts were also stained with a fibroblast marker, vimentin; representative images are provided in FIG. 3. The level of BrdU- and vimentin-double positive cells was expressed as the percentage of BrdU- and vimentin-double positive cells per total vimentin-positive cells (the BrdU/Vimentin Labeling Index), and the results were summarized in Table 2.

TABLE 2

| Treatment | BrdU/Vimentin Labeling Index (%) |
|---|---|
| UT | 1.9 ± 0.63 |
| 29-mer | 9.6 ± 1.6* |
| 24-mer | 10.1 ± 1.9* |
| 20-mer | 10.4 ± 2.3* |
| 18-mer | 2.1 ± 0.61 |
| Mo 20-mer | 11.3 ± 1.6* |
| Mo 29-mer | 11.1 ± 2.0* |

*$P < 0.002$ versus untreated cells.

Collectively, dermal fibroblast cultivated in medium containing the PEDF-derived peptides according to embodiments of the present disclosure (e.g., 29-mer, 24-mer, 20-mer and two mouse homologous peptides) were more proliferative (about 5-fold) than those cultivated in control medium (Table 2). By contrast, the 18-mer without the "SLGA" residues treatment failed to elicit such effect.

Example 3.2

PEDF Peptides Promote Dermal Fibroblast Proliferation In Vivo

Specimens from Example 2, above, were also stained for the fibroblast marker, vimentin, and the vimentin-positive cells were counted under microscope.

TABLE 3

| Treatment | Vimentin+ Cells per mm² |
|---|---|
| Vehicle/CT | 1094 ± 86 |
| Vehicle/MN | 1126 ± 92 |
| 29-mer/MN | 1688 ± 197* |
| 20-mer/MN | 1745 ± 143* |

*$P < 0.002$ versus the vehicle/MN group.

The data in Table 3 indicates that the samples treated with 29-mer/MN and 20-mer/MN possess significantly higher numbers of fibroblasts in dermal area, as compared with those treated with vehicle/MN and vehicle alone (i.e., vehicle/CT). This observation suggests that the transdermal delivery of the present PEDF peptides is positively related to the fibroblast density in the dermis.

To investigate whether the transdermal delivery of the present PEDF peptides promotes the proliferation of dermal fibroblast in vivo, mice were intraperitoneally injected with BrdU and euthanized at 16 hours after the PEDF peptide/MN treatment or the vehicle/MN treatment. Skin sections were stained for vimentin (green) and BrdU (red). The level of BrdU- and vimentin-double positive cells was expressed as the percentage of BrdU- and vimentin-double positive cells per total vimentin-positive cells (the BrdU/Vimentin Labeling Index), and the results are summarized in Table 4.

TABLE 4

| Treatment | BrdU/Vimentin Labeling Index (%) |
|---|---|
| Vehicle/MN | 6.9 ± 0.07 |
| 29-mer/MN | 16.9 ± 1.9* |
| 20-mer/MN | 17.3 ± 3.2* |

*$P < 0.05$ versus the vehicle/MN group.

As could be seen in Table 4, in skin sections from the 29-mer/MN and 20-mer/MN groups, there are more proliferating fibroblasts, as compared with sections treated with the DMSO-containing ointment (vehicle/MN). This observation indicates that the transdermal delivery of the present synthetic peptides is effective in promoting the proliferative activity of dermal fibroblasts. This increased proliferation of dermal fibroblasts coincides with the finding that the collagen content is improved by the transdermal delivery of the present PEDF peptides (Table 1, above).

Example 3.3

PEDF Peptides Promote Dermal Fibroblast Proliferation in Photo Damaged Skin In Vivo UVB irradiation is known to cause fragmentation of the dermal collagen matrix, which induces cell-cycle arrest of fibroblast. In this working example, we investigate whether the transdermal delivery of the present PEDF peptides is effective in restoring the proliferation activity of fibroblasts that were damaged by UVB radiation.

Six-week-old female nude mice (BALB/cAnN.Cg-Foxn1nu/CrlNarl) were irradiated with ultraviolet B (UVB) on the back 5 times a week for an eight-week period using a bank of five UVB lamps (model XL-1000B, Spectrolinker™ apparatus; emission peak: 312 nm), placed about 20 cm above the backs of the animals. During the UVB exposure, the mice were allowed to move freely within the cage. The irradiation intensity represented as the minimal erythe al dose (MED) was set at 1 MED during the first 2 weeks (60 mJ/cm²), and was progressively elevated to 2

MED (120 mJ/cm$^2$) in the 3$^{rd}$-4$^{th}$ week, to 3 MED (180 mJ/cm$^2$) in the 5$^{th}$-6$^{th}$ week, and to 4 MED (240 mJ/cm$^2$) during the 7$^{th}$-8$^{th}$ weeks of the experiment. After the 8-week UVB exposure, animals developed noticeable wrinkles and were subsequently randomly divided into the following 4 groups, with 3 mice in each group. In the UVB/vehicle, UVB/29-mer, UVB/20-mer, and UVB/18-mer groups, 350 μl of ointment (containing DMSO, 29-mer, 20-mer or 18-mer PEDF) was applied to the dorsal skin and then transdermal delivery was achieved by punching the ointment treated skin with the microneedle patch. Also, mice that were not subjected to UVB radiation were used as control (Normal). The ointment/microneedle treatment was given twice a week for 2 weeks. Mice were intraperitoneally given BrdU and euthanized at 16 hours after the last treatment. Skin sections were stained for vimentin and BrdU. The level of BrdU- and vimentin-double positive cells was expressed as the percentage of BrdU- and vimentin-double positive cells per total vimentin-positive cells (the BrdU/Vimentin Labeling Index). Quantitative results were summarized in Table 5.

TABLE 5

| Treatment | BrdU/Vimentin Labeling Index (%) |
|---|---|
| Normal | 4.1 ± 0.8 |
| UVB/vehicle | 2.1 ± 1.1* |
| UVB/29-mer | 5.2 ± 1.9** |
| UVB/20-mer | 5.9 ± 1.3** |
| UVB/18-mer | 2.0 ± 0.8 |

*P < 0.01 versus the Normal group;
**P < 0.05 versus the UVB/vehicle group.

As could be seen in Table 5i exposure reduced the proliferative activity of dermal fibroblast by about 50%, as compared with the skins that were not exposed with UVB radiation (UVB/vehicle: 2.1±1.1% versus Normal: 4.1±0.8%). On the other hand, the transdermal delivery of 29-mer and 20-mer after the UVB exposure enhanced the proliferative activity of dermal fibroblasts by about 2.5-fold, as compared with that of the UVB/vehicle group. It is noted that the proliferative activity in the 29-mer or 20-mer treated animals is even higher than that of animals not irradiated by UVB, although the difference is less significant. In contrast, the 18-mer that is missing the important "SLGA residues" failed to promote the dermal fibroblast proliferation.

In conclusion, data presented in Example 3 (including Examples 3.1 to 3.3) demonstrated that the present PEDF peptides were effective in promoting the proliferation of dermal fibroblast in normal skin tissues (i.e., those not treated with UVB radiation), as well as in photo-damaged skin tissues (i.e., those treated with UVB radiation and with noticeable wrinkles resulted from the exposure). Since fibroblasts are responsible for collagen synthesis, the improved proliferative activity of the fibroblasts and resulting higher fibroblast density may in turn promote the collagen synthesis. Therefore, the present PEDF peptides are capable of evoking the intrinsic repair mechanisms of the skin for collagen synthesis.

Example 4

PEDF Peptide Reduce UVB-Induced MMP-1 Expression

MMP-1 (interstitial collagenase) is the only enzyme capable of catalyzing the cleavage of the collagen triple helix in type I and III collagens. Moreover, MMP-1 is the major collagenolytic enzyme present in human skin and upregulated in response to UV irradiation. Rodents lack the MMP-1 gene, which is functionally replaced in these animals by MMP-13. Hence, the present working example aims to elucidate whether the present synthetic peptide reduce the MMP-1 and MMP-13 expression induced by UVB exposure.

According to our preliminary study, cell viability was greater than 95% relative to that of the control after exposure to 15 mJ/cm$^2$ UVB irradiation (data not shown). Human dermal fibroblasts (WS-1 cells) and primary mouse dermal fibroblasts pretreated with 100 nM 29-mer for 24 hours did not cause any significant change in cell viability (data not shown) and did not cause any significant change in cell migration assayed by a transwell assay (data not shown). We also found that UV irradiation at this dose led to an increase in MMP expression levels. Therefore, the exposure dose was set at 15 mJ/cm$^2$ in the following experiment.

WS-1 were seeded on a six-well plate at a density of 1×10$^5$ cells per well and grown in the 10% FBS-DMEM growth medium for 24 hours and then incubated with 1% FBS-DMEM supplemented with or without 100 nM PEDF peptide for further 24 hours. The cells were washed twice with phosphate buffered saline (PBS) and exposed to UVB radiation covered with PBS. The UVB treatment was conducted in a cell culture hood by using a UVB lamp (model XL-1000B, Spectrolinker™ Inc.) at a final dose of 15 mJ/cm$^2$ for about 100 seconds. Cell viability was assayed using trapan blue exclusion assay (>95%). After UVB irradiation, PBS was replaced with 1% FBS-DMEM with or without PEDF peptide for further 48 hours and then protein extracts were assayed by western blotting for the expression of MMP-1 protein. Cells that were not subjected to UVB irradiation were used as control (normal). The expression level of MMP-1 was normalized with the expression level in the Vehicle/UVB group (set to 100%), and quantitative results are summarized in Table 6.

TABLE 6

| Treatment | MMP-1 Expression Level (%) |
|---|---|
| Normal | 5 ± 1.2 |
| 29-mer | 5 ± 2.3 |
| Vehicle/UVB | 100 |
| 29-mer/UVB | 42 ± 3.3* |
| 24-mer/UVB | 48 ± 7.2* |
| 20-mer/UVB | 50 ± 5.1* |

*P < 0.02 versus the vehicle/UVB group.

By comparing the vehicle/UVB and normal groups, we notice that UVB irradiation results in a significant increase in MMP-1 protein expression (100% versus about 5% in the normal group). However, pre-incubation of fibroblasts with 29-mer, 24-mer or 20-mer significantly reduces the MMP-1 protein levels to about half of the vehicle/UVB group.

Primary mouse dermal fibroblasts in passage 2 of monolayer cultures were incubated with 1% FBS-DMEM supplemented with or without 100 nM PEDF peptide for 24 hours, and then subjected to UVB irradiation as described above. After UVB irradiation, PBS was replaced with 1% FBS-DMEM with or without PEDF peptide for further 24 hours, and then cellular total RNAs were extracted for subsequent RT-PCR analysis. The expression level of MMP-13 mRNA was normalized with the expression level in the Vehicle/UVB group (set to 100%), and quantitative results are summarized in Table 7.

TABLE 7

| Treatment | MMP-13 Expression Level (%) |
|---|---|
| Normal | 5.5 ± 0.65 |
| 29-mer | 4.8 ± 0.63 |
| Vehicle/UVB | 100 ± 0.0 |
| 29-mer/UVB | 15.8 ± 1.8* |
| 24-mer/UVB | 16.3 ± 1.5* |
| 20-mer/UVB | 15.8 ± 3.3* |
| 18-mer/UVB | 103.3 ± 7.8 |

*$P < 0.0001$ versus the vehicle/UVB group.

Similar to the finding above in Table 6, the expression level of MMP-13 was also up-regulated by UVB exposure (the vehicle/UVB group versus the normal group). Also, such upregulation was substantially reduced in cells pre-treated with the present PEDF peptides (29-mer/UVB, 24-mer/UVB, and 20-mer/UVB versus vehicle/UVB). In contrast, the 18-mer without the "SLGA residues" was unable to reduce the UVB-induced upregulation.

These results suggest that the present PEDF peptides may protect human dermal fibroblast against UVB-induced MMP-1 induction. Breakdown of type I collagen by MMP-1 is a key contributing factor to photoaging. Therefore the present PEDF peptides may be used as an anti-photoaging agent.

Example 5

PEDF Peptide Reduces UV-Induced Wrinkles

Formation of wrinkles is closely related to repetitive exposure to UVB irradiation. Specifically, UVB irradiation induces collagen destruction and inhibits procollagen biosynthesis in dermis; which result in collagen loss and hence wrinkle formation. In this working example, we investigated the anti-wrinkle effect of present PEDF peptides in nude (i.e, hairless) mice. Wrinkles were induced by an eight-week UVB irradiation according to the procedure set forth in Example 3.3 above. The appearance of mice was photographed before the UVB irradiation (normal), after the UVB irradiation (UVB/UT) and after the 2-week treatment with the respective ointment (UVB/vehicle, UVB/29-mer, UVB/20-mer and UVB/18-mer); representative photographs are provided in FIG. 4.

Figure 4:
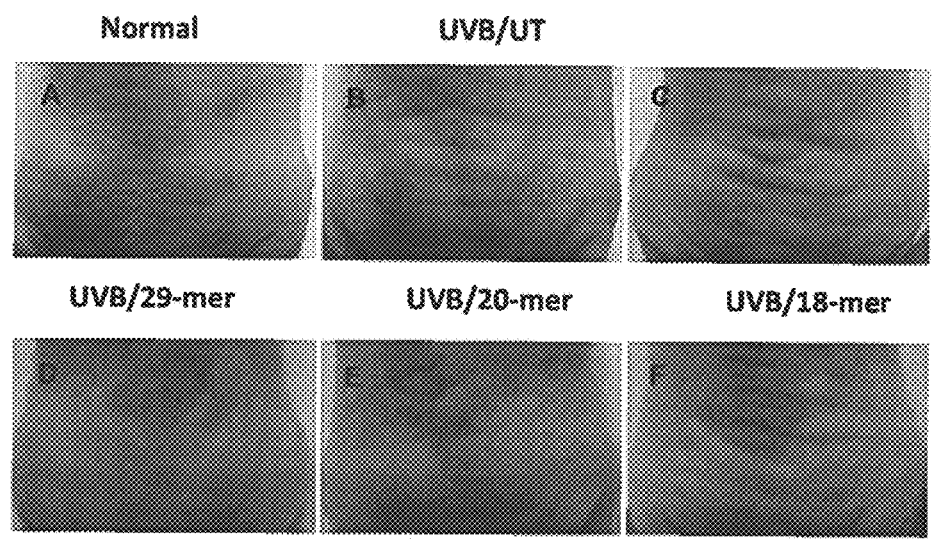
FIG. 4 provides representative photographs illustrating the wrinkle formation of mice in each experimental condition.

As illustrated in FIG. 4, mice developed noticeable amounts of deep and long wrinkles after UVB irradiation (normal group versus UVB/UT group). Mice treated with vehicle- or 18-mer-containing ointment also had deep and long wrinkles, indicating that 18-mer is not capable of reducing the wrinkles that had been formed as the result of UVB irradiation. By contrast, in mice treated with the present PEDF peptides (e.g., 29-mer and 20-mer), wrinkle lines were fewer and finer than those found in the UVB/UT, UVB/vehicle, and UVB/18-mer groups.

Figure 5:
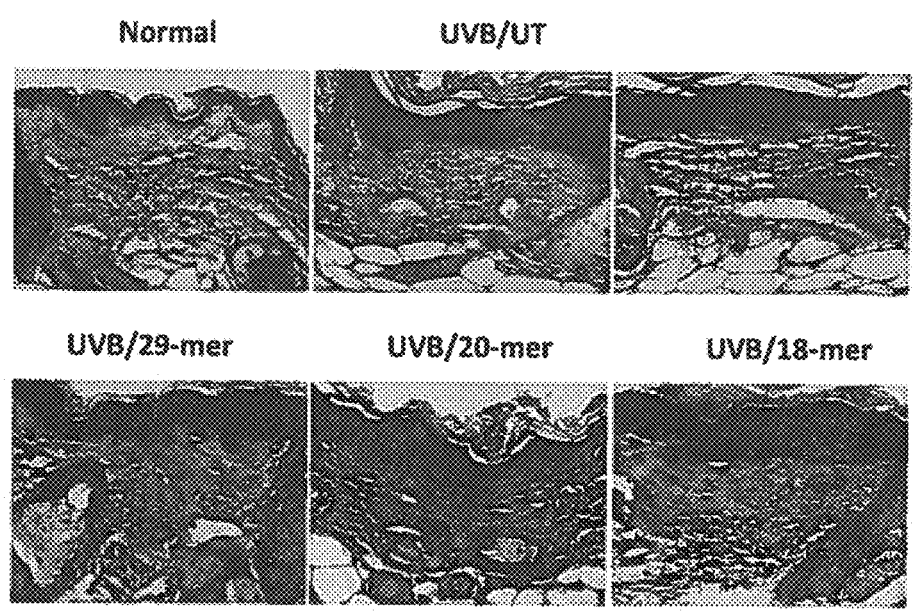
FIG. 5 provides representative images of skin tissue sections stained by Masson's trichrome to highlight the collagen fibres according to yet another working example of the present disclosure.

Skin specimens were subjected to Masson's trichrome staining to estimate the collagen contents thereof, and representative photographs are provided in FIG. 5 (original magnification ×200). The levels of type I collagen (COL1A1) were also investigated by immunoblot analysis, and the results were normalized with the level of the untreated normal group (set to 100%). Quantitative results are summarized in Table 8.

TABLE 8

| Treatment | COL1A1 Level (%) |
|---|---|
| Normal | 100 |
| UVB/UT | 45.0 ± 3.6* |
| UVB/vehicle | 47.3 ± 1.9 |
| UVB/29-mer | 91.0 ± 5.0** |
| UVB/20-mer | 92.3 ± 9.1** |
| UVB/18-mer | 45.0 ± 3.8 |

*$P < 0.0001$ versus the non-treated normal group.
**$P < 0.001$ versus the UVB/vehicle group Referring to both FIG. 5 and Table 8, it is found that repetitive UVB irradiation significantly decreased the collagen signal and COL1A1 level in the dermis (UVB/UT), as compared with that of the normal mice in the non-treated normal group. By contrast, transdermal delivery of the present PEDF peptides (e.g., in the UVB/29-mer and UVB/20-mer groups) significantly enhanced both collagen and COL1AL levels in the dermis, as compared with those in the UVB/vehicle group. These findings suggest that the transdermal delivery of the present PEDF peptides may induce collagen synthesis in UVB-damaged dermis, which may justify the reduced wrinkle formation in mice treated with present PEDF peptides.

The present disclosure is the first to demonstrate that transdermal delivery of short, synthetic PEDF peptides has protective effect against skin aging. As compared with the intravenous or intramuscular delivery of vectors expressing full-length PEDF peptides, transdermal delivery of short synthetic PEDF peptides is a safe and less expensive approach.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for ameliorating skin aging in a subject, comprising: administering topically or transdermally to the subject at the skin in need of treatment a synthetic peptide consisting of an amino add sequence having 20-39 amino acid residues in length, wherein the amino acid sequence at least includes a sequence selected from the group consisting of SEQ ID NOs: 1-3, 5, 6, 8 and 9.

2. The method of claim 1, wherein 4 consecutive residues of the synthetic peptide are identical to residues 11 . . . 14 of SEQ ID NO: 1.

3. The method of claim 1, wherein the skin aging is photoaging.

4. The method of claim 1, wherein the subject is a human.

5. The method according to claim 1, wherein the synthetic peptide is formulated as a pharmaceutical composition comprising,
an effective amount of the synthetic peptide; and
a pharmaceutically acceptable excipient.

6. The method of claim 5, wherein 4 consecutive residues of the synthetic peptide are identical to residues 11-14 SEQ ID NO: 1.

7. The method of claim 5, wherein the pharmaceutical composition is in the form of a solution, spray, aerosol, foam, cream, lotion, ointment, gel, or patch.

8. The method of claim 5, further comprising a penetration enhancer.

9. The method of claim 5, wherein the skin aging is photoaging.

10. The method of claim 5, wherein the subject is a human.

11. The method of claim 1, wherein the administering is by transdermally delivering the synthetic peptide to a dermis of the subject.

12. The method of claim 11, wherein 4 consecutive residues of the synthetic peptide are identical to residues 11-14 of SEQ ID NO: 1.

13. The method of claim 11, wherein the synthetic peptide is formulated into a pharmaceutical composition comprising the synthetic peptide and a pharmaceutically acceptable excipient.

14. The method of claim 13, wherein the pharmaceutical composition is in the foam of a solution, spray, aerosol, foam, cream, lotion, ointment, gel, or patch.

15. The method of claim 13, wherein the pharmaceutical composition is topically administered to the skin of the subject.

16. The method of claim 15, further comprising applying an external stimulus to the skin of the subject before, concurrently with, or after the topical administration of the pharmaceutical composition, whereby the transdermal delivery of the synthetic peptide is enhanced.

17. The method of claim 16, wherein the external stimulus is a mechanical, electrical, thermal, ultrasonic, or radio frequency stimulus.

18. The method of claim 16, wherein the pharmaceutical composition further comprises a penetration enhancer.

19. The method of claim 11, wherein the skin aging is photoaging.

20. The method of claim 11, wherein the subject is a human.

* * * * *